United States Patent [19]

Mizogami et al.

[11] 4,189,484
[45] Feb. 19, 1980

[54] ANTIHYPERTENSIVE QUINAZOLINE DERIVATIVES

[75] Inventors: Susumu Mizogami; Hidetoshi Hiranuma; Tetsuo Sekiya; Mitsuo Hanazuka, all of Ami, Japan

[73] Assignee: Mitsubishi Yuka Pharmaceutical Co., Ltd., Tokyo, Japan

[21] Appl. No.: 956,326

[22] Filed: Oct. 31, 1978

[30] Foreign Application Priority Data

Nov. 8, 1977 [JP] Japan .................................. 52-133105
Feb. 27, 1978 [JP] Japan .................................. 53-020891

[51] Int. Cl.$^2$ .................... A61K 31/505; C09B 23/16; C09B 55/00
[52] U.S. Cl. ........................................ 424/251; 542/427
[58] Field of Search ........................ 424/251; 542/427

[56] References Cited

U.S. PATENT DOCUMENTS 3,511,836 5/1970 Hess .................................. 424/251 X Primary Examiner—Leonard Schenkman
Attorney, Agent, or Firm—Frishauf, Holtz, Goodman & Woodward

[57] ABSTRACT

Novel quinazoline compounds and antihypertensive compositions containing said compounds are disclosed; said compounds having the formula:

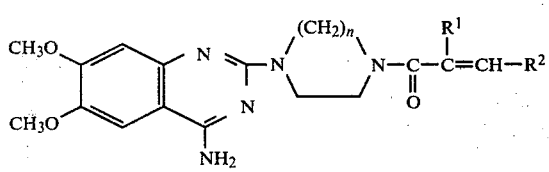

wherein
$R^1$ is a hydrogen atom or an alkyl group having 1-5 carbon atoms;
$R^2$ is a group of the formula

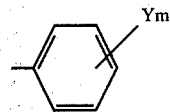

in which Y is a hydrogen atom, an alkyl group of 1-5 carbon atoms, an alkoxy group of 1-5 carbon atoms, an alkenyloxy group, a methylenedioxy group, a nitro group, a halogen atom, a trifluoromethyl group, an acyloxy group, a hydroxy group, an unsubstituted or substituted amino group or a condensed benzene nucleus and m is an integer of 1-3 inclusive, or a group of the formula

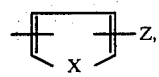

in which X is an oxygen atom, a sulfur atom or a carbon-nitrogen double bond and Z is a hydrogen atom, an alkyl group of 1-5 carbon atoms, an alkoxy group of 1-5 carbon atoms, a nitro group or a halogen atom; and n is an integer of 2-3 inclusive; provided that, when $R^2$ is the said group

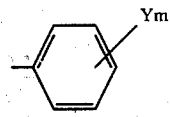

n is 2 and $R^1$ is a hydrogen atom or, when $R^2$ is the said group

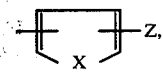

n is 2 or 3 and $R^1$ is a hydrogen atom or the said alkyl group and a pharmaceutically acceptable acid addition salt thereof.

38 Claims, No Drawings

ANTIHYPERTENSIVE QUINAZOLINE DERIVATIVES

This invention relates to a new group of quinazoline compounds and salts thereof, a process for preparing the same as well as their use as an antihypertensive drug.

More particularly, it is concerned with a novel quinazoline compound having the formula:

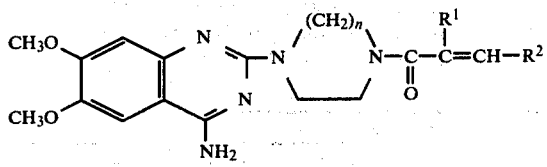

wherein
$R^1$ is a hydrogen atom or an alkyl group having 1-5 carbon atoms;
$R^2$ is a group of the formula

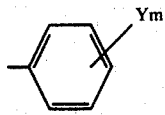

in which Y is a hydrogen atom, an alkyl group of 1-5 carbon atoms, an alkoxy group of 1-5 carbon atoms, an alkenyloxy group, a methylenedioxy group, a nitro group, a halogen atom, a trifluoromethyl group, an acyloxy group, a hydroxy group, an unsubstituted or substituted amino group or a condensed benzene nucleus and m is an integer of 1-3 inclusive, or a group of the formula

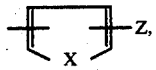

in which X is an oxygen atom, a sulfur atom or a carbon-nitrogen double bond and Z is a hydrogen atom, an alkyl group of 1-5 carbon atoms, an alkoxy group of 1-5 carbon atoms, a nitro group or a halogen atom; and
n is an integer of 2-3 inclusive;
provided that, when $R^2$ is the said group

n is 2 and $R^1$ is a hydrogen atom or, when $R^2$ is the said group

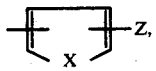

n is 2 or 3 and $R^1$ is a hydrogen atom or the said alkyl group and a pharmaceutically acceptable acid addition said thereof. Also, it is concerned with a process for preparing the quinazoline compound (I) and with an antihypertensive composition containing as an active ingredient the quinazoline compound (I).

In the prior art, U.S. Pat. No. 3,511,836 discloses the quinazoline derivative having the non-proprietary name "Prazosin," the following structure and its antihypertensive effect:

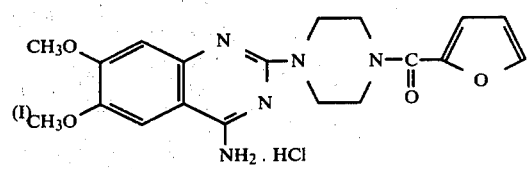

Moreover, there have been proposed various analogous quinazoline derivatives with antihypertensive action, for instance, in Japanese Patent Publication No. 22135/1970; Japanese Published Unexamined Patent Applications No. 80877/1976, No. 93987/1975, No. 66690/1974, No. 66691/1974, No. 100479/1977, No. 140474/1975, No, 82285/1976, No. 48678/1977, No. 48681/1977 and No. 102286/1977; and so on.

It is also reported that the prior art compounds, particularly prazosin, might exert an antihypertensive action upon adrenergic α-receptor blocking effect and peripheral vasodilating effect, simultaneously with considerable side effects [Bendall, et al, Brit. Med. J. 2, 727 (1975): Ress, et al., ibid, 3, 593 (1975): Sead, et al., ibid, 3, 305 (1975): Gabriel, et al., Lancet 1, 1095 (1975): Rosendorff, Brit. Med. J. 2, 508 (1976)]. It is said that such side effects may be led from a rapid reduction of blood pressure (Committee on Safety of Medicines, Adverse reactions series No. 12, London, DHSS, 1975).

The present inventors have made earnest studies for quinazoline derivatives with more excellent antihypertensive effects in more safety and, as a result, found that the quinazoline compounds having the above formula (I) are new substances not disclosed in the prior art including the above-recited literatures and they can show a superior antihypertensive activity. This invention has been, accordingly, completed upon the above findings.

It is a primary object of this invention to provide new quinazoline compounds (I) having a valuable pharmacological property.

Another object of this invention is to provide a process for preparing the quinazoline compound (I).

Still another object of this invention is to provide an antihypertensive composition which contains as an active ingredient one or more of the quinazoline compounds (I).

These objects and other advantages of this invention will be apparent to those skilled in the art from the description as stated hereinbelow.

In one aspect of this invention, there is provided new class of the quinazoline compounds (I). It is to be noted that not only the quinazoline compounds (I) but pharmaceutically acceptable acid addition salts thereof are contemplated in this invention. The pharmaceutically acceptable acid addition salts of this invention are meant to be those salts which do not substantially enhance the toxicity of a basic compound and these acid addition salts are of a particular significance for treating hypertension. The acid addition salts may include those with a mineral acid, e.g. hydrochloric acid, hydroiodic acid, hydrobromic acid, phosphoric acid, metaphosphoric acid, nitric acid or sulfuric acid and with an organic acid, e.g. formic acid, acetic acid, propionic acid, phenylacetic acid, tartaric acid, citric acid, malic acid, benzoic acid, glycolic acid, glucuronic acid, gluconic acid, gulonic acid, succinic acid, lactic acid, ascorbic acid, fumaric acid, maleic acid, anthranilic acid, salicylic acid, methanesulfonic acid or an aryl sulfonic acid (e.g. p-toluenesulfonic acid.)

In the definitions of the above formula (I), $R^1$ may be exemplified by a hydrogen atom or an alkyl group having 1–5 carbon atoms such as a methyl, ethyl, n-propyl, isopropyl, n-butyl, isobutyl or n-pentyl group. Y may be exemplified by a hydrogen atom; the above alkyl group; an alkoxy group having 1–5 carbon atoms such as a methoxy, ethoxy, propoxy, isopropoxy, butoxy, isobutoxy or pentoxy group; an alkenyl group such as an allyloxy, crotyl (or 2-butenyl)oxy or methallyl-(2-methylallyl)oxy group; a methylenedioxy group; a nitro group; a halogen atom such as fluorine, chlorine or bromine; a trifluoromethyl group; an acyloxy group such as an acetoxy, propionyloxy or butyryloxy group; a hydroxy group; an amino group optionally substituted with $C_1$-$C_5$ alkyl or other group such as an amino, methylamino, ethylamino, dimethylamino or diethylamino group; or a condensed benzene nucleus such as a naphthyl group. In view of the number of m of 1–3, the substituent(s) Y(m) may be located at the 2-, 3- or 4-position; the 2 and 3–6 positions, the 3- and 4-positions or the 3- and 5-positions; or the 2-, 3- and 4-positions, 2-, 3- and 5-positions or the 3-, 4- and 5-positions in the phenyl ring. The substituent Z may be a hydrogen atom; the above alkyl group; the above alkoxy group; a nitro group; or a halogen atom. Where X is an oxygen atom, a sulfur atom and a carbon-nitrogen double bond, the group

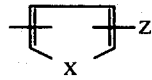

stands for a furan ring, a thiophene ring and a pyridine ring, respectively. The furan or thiophene ring may be linked with the acryloyl moiety at the 2- or 3- position thereof and the pyridine ring with the acryloyl moiety at the 2-, 3- or 4-position thereof, while the substituent Z may be located in the ring at any suitable position except for the position to which the acryloyl moiety is attached.

More specifically, the quinazoline compounds of this invention comprise those of the formula (I) wherein $R^1$ is a hydrogen atom, $R^2$ is the above-defined group

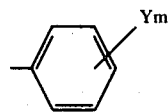

and n is 2 and those of the formula (I) wherein $R^1$ is a hydrogen atom or the above alkyl group, $R^2$ is the above group

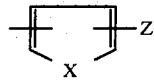

and n is 2 or 3.

Representative examples of the present quinazoline compounds (I) are listed hereinbelow. The compound No. allotted to the individual quinazoline compound will be frequently referred to hereunder.

| Compound No. | Chemical Name |
| --- | --- |
| 1. | 2-(4-Cinnamoylpiperazin-1-yl)-4-amino-6,7-dimethoxyquinazoline |
| 2. | 2-[4-(2-Methylcinnamoyl)-piperazin-1-yl]-4-amino-6,7-dimethoxyquinazoline |
| 3. | 2-[4-(3-Methylcinnamoyl)-piperazin-1-yl]-4-amino-6,7-dimethoxyquinazoline |
| 4. | 2-[4-(4-Methylcinnamoyl)-piperazin-1-yl]-4-amino-6,7-dimethoxyquinazoline |
| 5. | 2-[4-(4-Isopropylcinnamoyl)-piperazin-1-yl]-4-amino-6,7-dimethoxyquinazoline |
| 6. | 2-[4-(2-Methoxycinnamoyl)-piperazin-1-yl]-4-amino-6,7-dimethoxyquinazoline |
| 7. | 2-[4-(3-Methoxycinnamoyl)-piperazin-1-yl]-4-amino-6,7-dimethoxyquinazoline |
| 8. | 2-[4-(4-Methoxycinnamoyl)-piperazin-1-yl]-4-amino-6,7-dimethoxyquinazoline |
| 9. | 2-[4-(2-Ethoxycinnamoyl)-piperazin-1-yl]-4-amino-6,7-dimethoxyquinazoline |
| 10. | 2-[4-(4-Ethoxycinnamoyl)-piperazine-1-yl]-4-amino-6,7-dimethoxyquinazoline |
| 11. | 2-[4-(4-Butoxycinnamoyl)-piperazin-1-yl]-4-amino-6,7-dimethoxyquinazoline |
| 12. | 2-[4-(3,4-Dimethoxycinnamoyl)-piperazin-1-yl]-4-amino-6,7-dimethoxyquinazoline |
| 13. | 2-[4-(3,5-Dimethoxycinnamoyl)-piperazin-1-yl]-4-amino-6,7-dimethoxyquinazoline |
| 14. | 2-[4-(2,3,4-Trimethoxycinnamoyl)-piperazin-1-yl]-4-amino-6,7-dimethoxyquinazoline |
| 15. | 2-[4-(3,4,5-Trimethoxycinnamoyl)-piperazin-1-yl]-4-amino-6,7-dimethoxyquinazoline |
| 16. | 2-[4-(3,4-Methylenedioxycinnamoyl)-piperazin-1-yl]-4-amino-6,7-dimethoxyquinazoline |
| 17. | 2-[4-(4-Allyloxycinnamoyl)-piperazin-1-yl]-4-amino-6,7-dimethoxyquinazoline |
| 18. | 2-[4-(3-Nitrocinnamoyl)-piperazin-1-yl]-4-amino-6,7-dimethoxyquinazoline |
| 19. | 2-[4-(4-Chlorocinnamoyl)-piperazin-1-yl]-4-amino-6,7-dimethoxyquinazoline |
| 20. | 2-[4-(3,4-Dichlorocinnamoyl)-piperazin-1-yl]-4-amino-6,7-dimethoxyquinazoline |
| 21. | 2-[4-(4-Bromocinnamoyl)-piperazin-1-yl]-4-amino-6,7-dimethoxyquinazoline |
| 22. | 2-[4-(3-Trifluoromethylcinnamoyl)-piperazin-1-yl]-4-amino-6,7-dimethoxyquinazoline |
| 23. | 2-[4-(4-Dimethylaminocinnamoyl)-piperazin-1-yl]-4-amino-6,7-dimethoxyquinazoline |
| 24. | 2-[4-(4-Acetoxycinnamoyl)-piperazin-1-yl]-4-amino-6,7-dimethoxyquinazoline |
| 25. | 2-[4-(4-Hydroxycinnamoyl)-piperazin-1-yl]-4-amino-6,7-dimethoxyquinazoline |
| 26. | 2-{4-[3-(α-Naphthyl)acryloyl]-piperazin-1-yl}-4-amino-6,7-dimethoxyquinazoline |
| 27. | 2-[4-(4-Isopropyloxycinnamoyl)-piperazin-1-yl]-4-amino-6,7-dimethoxyquinazoline |
| 28. | 2-{4-[3-(Furan-2-yl)-acryloyl]-piperazin-1-yl}-4-amino-6,7-dimethoxyquinazoline |
| 29. | 2-{4-[3-(Furan-3-yl)-acryloyl]-piperazin-1-yl]-4-amino-6,7-dimethoxyquinazoline |
| 30. | 2-{4-[3-(5-Methylfuran-2-yl)-acryloyl]-piperazin-1-yl}-4-amino-6,7-dimethoxyquinazoline |

-continued

| Compound No. | Chemical Name |
|---|---|
| 31. | 2-{4-[2-Methyl-3-(furan-2-yl)-acryloyl]-piperazin-1-yl}-4-amino-6,7-dimethoxyquinazoline |
| 32. | 2-{4-[3-(5-Methoxyfuran-2-yl)-acryloyl]-piperazin-1-yl}-4-amino-6,7-dimethoxyquinazoline |
| 33. | 2-{4-[3-(5-Nitrofuran-2-yl)-acryloyl]-piperazin-1-yl}-4-amino-6,7-dimethoxyquinazoline |
| 34. | 2-{4-[3-(5-chlorofuran-2-yl)-acryloyl]-piperazin-1-yl}-4-amino-6,7-dimethoxyquinazoline |
| 35. | 2-{4-[3-(Thiophen-2-yl)-acryloyl]-piperazin-1-yl}-4-amino-6,7-dimethoxyquinazoline |
| 36. | 2-{4-[3-(Thiophen-3-yl)-acryloyl]-piperazin-1-yl}-4-amino-6,7-dimethoxyquinazoline |
| 37. | 2-{4-[3-(3-Methylthiophen-2-yl)-acryloyl]-piperazin-1-yl}-4-amino-6,7-dimethoxyquinazoline |
| 38. | 2-{4-[3-(5-Methylthiophen-2-yl)-acryloyl]-piperazin-1-yl}-4-amino-6,7-dimethoxyquinazoline |
| 39. | 2-{4-[2-Methyl-3-(thiophen-2-yl)-acryloyl]-piperazin-1-yl}-4-amino-6,7-dimethoxyquinazoline |
| 40. | 2-{4-[3-(5-Methoxythiophen-2-yl)-acryloyl]-piperazin-1-yl}-4-amino-6,7-dimethoxyquinazoline |
| 41. | 2-{4-[3-(5-Nitrothiophen-2-yl)-acryloyl]-piperazin-1-yl}-4-amino-6,7-dimethoxyquinazoline |
| 42. | 2-{4-[3-(5-Chlorothiophen-2-yl)-acryloyl]-piperazin-1-yl}-4-amino-6,7-dimethoxyquinazoline |
| 43. | 2-{4-[3-(Pyridin-2-yl)-acryloyl]-piperazin-1-yl}-4-amino-6,7-dimethoxyquinazoline |
| 44. | 2-{4-[3-(Pyridin-3-yl)-acryloyl]-piperazin-1-yl}-4-amino-6,7-dimethoxyquinazoline |
| 45. | 2-{4-[3-(Pyridin-4-yl)-acryloyl]-piperazin-1-yl}-4-amino-6,7-dimethoxyquinazoline |
| 46. | 2-{4-[3-(Furan-2-yl)-acryloyl]-homopiperazin-1-yl}-4-amino-6,7-dimethoxyquinazoline |
| 47. | 2-{4-[3-(Thiophen-2-yl)-acryloyl]-homopiperazin-1-yl}-4-amino-6,7-dimethoxyquinazoline |
| 48. | 2-{4-[3-(Pyridin-3-yl)-acryloyl]-homopiperazin-1-yl}-4-amino-6,7-dimethoxyquinazoline |

Of the above-recited compounds, there may be mentioned as a preferable group in view of pharmacological properties those compounds having Compound Nos. 1, 2, 3, 4, 5, 7, 8, 10, 13, 14, 16, 17, 21, 22, 23, 28, 29, 30, 31, 33, 34, 35, 36, 37, 38, 39, 41, 42, 43, 44, 45, 46, 47 and 48. The more preferable group includes those compounds having Compound Nos. 1, 2, 3, 8, 10, 28, 35, 36, 39 and 43.

In another aspect of this invention, the quinazoline compound (I) can be prepared by any of the processes as schematically shown below:

Process A

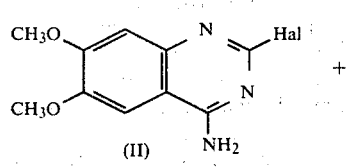

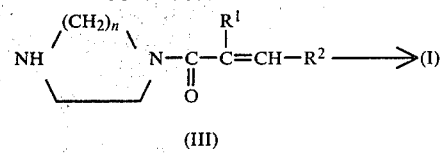

In the formulae, Hal represents a halogen atom, particularly a chlorine or bromine atom and $R^1$, $R^2$ and n are as defined above. The reaction in Process A may be conducted in the absence of a solvent or in the presence of a solvent that does not participate in the reaction. As the solvent which may be employed, there may be an aromatic hydrocarbon such as benzene, toluene or xylene; an ether such as ethyl ether, tetrahydrofuran or dioxane; an alcohol such as ethanol, propanol or amyl alcohol; a ketone such as acetone or methyl ethyl ketone; ethyl acetate; dimethylformamide; dimethylacetamide; or dimethyl sulfoxide. The reaction may be effected at 50°–200° C., preferably 70°–150° C. for 1–24 hours, preferably 2–8 hours. The starting material (II) and the reagent (III) may be used in a molar ratio of 1:not less than 1, preferably of 1:1–2. The reaction may proceed more smoothly by the use of an acid binding agent, e.g. triethylamine, N-methylmorpholine, pyridine, 1,8-diazabicyclo[5.4 0]undecene-7, an alkali bicarbonate, an alkali carbonate or an excess amount of the reagent (III). The starting material (II) and its preparation are described in U.S. Pat. No. 3,511,836 and the reagent (III) may be easily prepared by condensing piperazine or homopiperazine salt with the corresponding cinnamic or acrylic acid derivative.

As to piperazine monosalt or homopiperazine monosalt, there can be mentioned an inorganic acid salt thereof such as hydrochloric acid, hydrobromic acid, sulphuric acid and phosphoric acid or an organic acid salt thereof such acetic acid, maleic acid and benzoic acid. But the hydrobromic acid salt is preferred.

As to reactive derivatives of various cinnamic or acrylic acids, there can be mentioned acid halides such as chloride, and bromides, acid anhydrides of various cinnamic or acrylic acids, mixed anhydrides consisting of various cinnamic or acrylic acids and various halogenated carbonic ester such as methyl chlorocarbonate, ethyl chlorocarbonate, and isobutyl chlorocarbonate.

As to solvents used for this reaction, there can be used aromatic hydrocarbons such as benzene, toluene et al, alcohols such as methanol, ethanol, et al, ethers such as diethyl ether, tetrahydrofuran, dioxane et al, water, ethyl acetate, dimethylformamide and dimethylsulfoxide. A mixed solvent of the above solvents can be used.

According to the above reaction, there can be provided the following compounds: cinnamoylpiperazine, 2-methylcinnamoylpiperazine, 3-methylcinnamoylpiperazine, 4-methylcinnamoylpiperazine, 4-isopropylcinnamaylpiper, 2-methoxypiperazine, 3-methoxycinnamoylpiperazine, 4-methoxycinnamoylpiperazine, 2-ethoxycinnamoylpiperazine, 4-ethoxycinnamoylpiperazine, 4-isopropoxycinnamoylpiperazine, 4-butoxycinnoylpiperazine, 3,4-dimethoxycinnamoylpiperazine, 3,5-dimethoxycinnoulpiperazine, 2,3,4-trimethoxycinnamoylpiperazine, 3,4,5-trimethoxycinnomaylpiperazine, 3,4-methylenedioxycinnamoylpiperazine, 4-allyloxycinnomaylpiperazine, 3-chlorocinnamoylpiperazine, 4-bromocinnamylpiperazine, 3-(2-naphthyl)acryloylpiperazine, 3-(furan-2-yl)-acryloylpiperazine, 3-(furan-3-yl)acryloylpiperazine, 3-(5-methylfuran-2- yl)-acryloylpiperazine, 2-methyl-3-(furan-2-yl)-acryloylpiperazine, 3-(5-nitrofuran-2-yl)-acryloylpiperazine, 3-(5-chlorofuran-2-yl)-acryloylpiperazine, 3-(thiophen-2-yl)acryloylpiperazine, 3-(thiophen-3-yl)-

Alternatively, the present quinazoline compound (I) may be prepared through the synthetic route to form the quinazoline ring later as schematically shown thereinbelow:

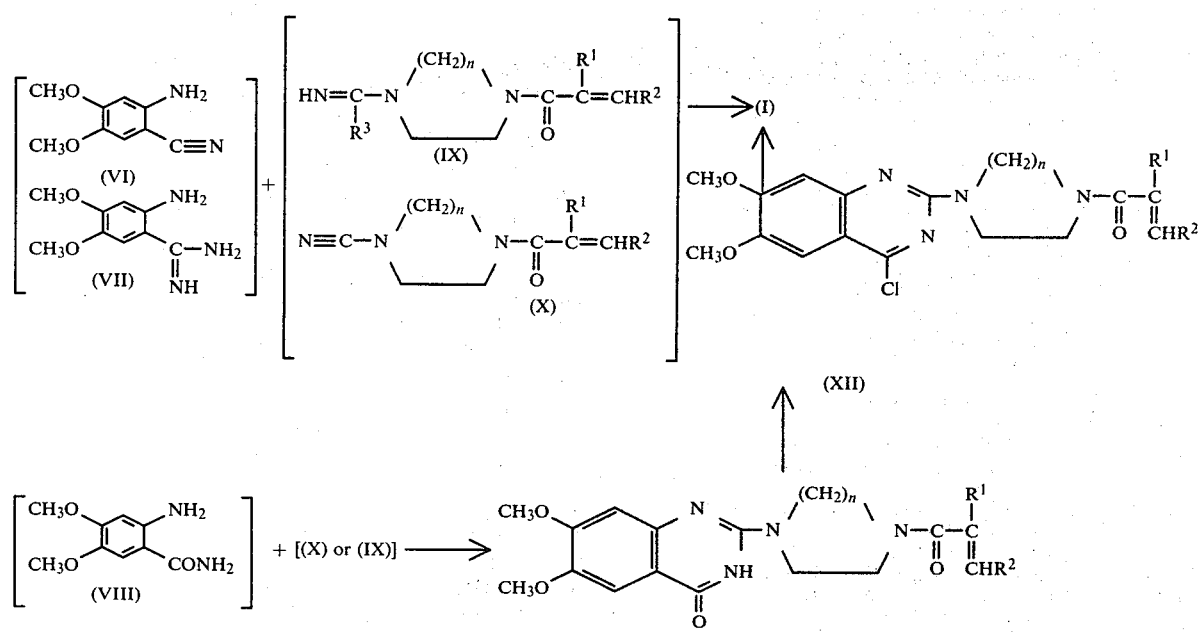

acryloylpiperazine, 3-(3-methylthiophen-2-yl)-acryloylpiperazine, 3-(5-methylthiophen-2-yl)-acryloylpiperazine, 2-methyl-3-(thiophen-2-yl)-acryloylpiperazine, 3-(5-nitrothiophen-2-yl)-acryloylpiperazine, 3-(5-chlorothiophen-2-yl)-acryloylpiperazine, 3-(pyridin-2-yl)-acryloylpiperazine, 3-(pyridin-3-yl)-acryloylpiperazine, 3-(pyridin-4-yl)-acryloylpiperazine, 3-(furan-2-yl)-acryloylhomopiperazine, 3-(thiopehn-2-yl)acryloylhomopiperazine, 3-(pyridin-3-yl)-acryloylhomopiperazine et al.

Process B

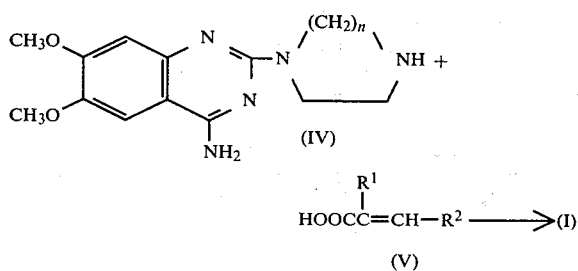

In the formulae, $R^1$, $R^2$ and n are as defined above. The Process B comprises reaction of the starting material (IV) with the acid derivative (V) or its reactive derivative. The reaction may be conducted in the same manner as explained above in the Process A. Reaction temperature, period, amounts of reagents, acid binding agents are similarly applied as set forth above. The starting material (IV) and its preparation are described in U.S. Pat. No. 4,001,237 or Japanese Published Unexamined Patent Application No. 66690/1974. The reactive derivatives of the acid derivative (V) may include the corresponding acid halide, acid anhydride, mixed anhydride, active ester and the like.

In the formulae, $R^3$ is —$NH_2$, —O—Alkyl or —S—alkyl and $R^1$, $R^2$ and n are as defined above.

The reaction may be effected by the use of any combination of one compound selected from compounds (VI), (VII) and (VIII) with one compound selected from compounds (X) and (IX) to produce the quinazoline compound (I) or the compound (XI), according to the well-known reaction procedures for preparing 2-substituted quinazoline derivatives (Japanese Patent Publication No. 22135/1970 or Japanese Published Unexamined Patent Applications No. 42775/1972 and No. 93987/1975). The reaction may be carried out in the absence of a solvent or in the presence of a solvent that does not participate in the reaction under heating. The same sort of solvents as named above in the Process A may be suitably adopted. The reaction can be more smoothly effected in the further presence of a base, e.g. triethylamine, pyridine, a metal hydride, an alcoholate, phenyl lithium or butyl lithium. Where the alcoholate is used as a base, there may be employed as a solvent an alcohol, e.g. ethanol, propanol or amyl alcohol.

The compound (XI) may be converted to the quinazoline compound (I) by a conventional halogenation with, for example, phosphorus oxychloride, phosphorus pentachloride or phosphorus pentabromide to form the compound (XII) and subsequent reaction with ammonia.

The quinazoline compound (I) produced according to the above processes may be obtained in the form of either a free base or a pharmaceutically acceptable salt upon the particular process employed. Conversion of the free base to the salt may be made in a usual manner, and vice versa.

Pharmacological activities and toxicities of the present quinazoline compounds are illustrated hereunder.

A. Antihypertensive effect

Antihypertensive effect was determined by oral administration of the test compound to spontaneously hypertensive rats (hereinafter referred to as SHR).

Female and male SHR 20–30 weeks of age, having systolic blood pressure of not less than 150 mmHg by a plethysmographic tail method, were used in the experiment. These SHR were anesthetized with ether and chronically embedded with a cannula for determination of blood pressure so that one end of the said cannula may be placed in abdominal aorta and the other end thereof may be projected out of dorsal neck. When rats regained their body weight before operation in more than 1 week from operation, the test compound was given. Determination was made by measuring a mean blood pressure and a heart rate under unanesthetized and unrestrained conditions with the cannula connected to an electronic recording system. The test compound was suspended in a 1% tragacanth gum solution to make up a concentration so as to be a volume of 5 ml./kg. and then orally given. Blood pressure and heart rate was measured after 1, 3, 6 and 24 hours from the administration.

The results are summarized in the following Tables 1, 2 and 3.

Table 1.

Antihypertensive effect (SHR, p.o.)

| Illustrated Compound No. | Dose (mg/kg., p.o.) | No. of animals | Blood pressure before administration (mmHg) | Change in blood pressure after 3 hrs. from administration (mmHg) |
|---|---|---|---|---|
| 1 | 10 | 3 | 174 | −53 |
|   | 1  | 4 | 176 | −18 |
| 2 | 10 | 3 | 187 | −43 |
| 3 | 10 | 3 | 185 | −35 |
| 4 | 10 | 3 | 172 | −18 |
| 5 | 10 | 3 | 167 | −12 |
| 7 | 10 | 3 | 167 | −18 |
| 8 | 10 | 3 | 157 | −25 |
| 10 | 10 | 3 | 190 | −53 |
|   | 1  | 3 | 180 | −19 |
| 13 | 10 | 3 | 177 | −12 |
| 14 | 10 | 3 | 170 | −22 |
| 16 | 10 | 3 | 155 | −13 |
| 17 | 10 | 3 | 177 | −18 |
| 21 | 10 | 3 | 170 | −22 |
| 22 | 10 | 3 | 182 | −10 |
| 23 | 10 | 3 | 163 | −15 |

Table 2

Antihypertensive effect of Compound No. 1 (SHR[1], p.o.)

| Test compound | Dose mg./kg. p.o. | Level before administration BP[2] (mm.Hg.) | Level before administration HR[3] (no/min.) | 1 hr. BP (mm.Hg.) | 1 hr. HR (no/min.) | 3 hrs. BP (mm.Hg.) | 3 hrs. HR (no/min.) | 6 hrs. BP (mm.Hg.) | 6 hrs. HR (no/min.) | 24 hrs. BP (mm.Hg.) | 24 hrs. HR (no/min.) |
|---|---|---|---|---|---|---|---|---|---|---|---|
| Control (1% Tragacanth 5 mg./kg.) | — | 170±1.6 | 404±16 | −5±3.9 | −4.6±4.9 | −1±1.9 | −2.5±5.5 | 2±2.5 | 3.7±5.7 | 0±3.5 | 9.6±2.7 |
| Compound No. 1 | 0.3 | 178±6.0 | 374±18 | −14±5.1* | −5.3±3.9 | −16±3.3** | −3.8±7.4 | −19±1.9* | 0.3±5.9 | 4±4.3 | 3.9±7.1 |
|  | 1 | 187±2.5 | 423±21 | −20±1.6** | −4.8±4.1 | −26±3.3** | −1.5±4.7 | −27±4.1** | −7.9±2.7 | −2±1.2 | −0.5±3.2 |
|  | 3 | 176±1.9 | 358±24 | −40±3.5** | 6.9±5.4 | −35±4.4** | −1.7±5.5 | −35±3.5** | 10.0±8.3 | −4±4.3 | 19.5±7.2 |
| Prazosin | 0.3 | 180±7.6 | 428±19 | −34±5.6** | 6.3±3.3 | −25±3.5** | 5.3±4.6 | −27±4.4** | 3.2±3.0 | −1±4.3 | 4.3±4.9 |
|  | 1 | 184±2.9 | 410±20 | −46±2.9** | 7.0±4.4 | −37∓1.2** | 1.5±2.8 | −31±2.9** | −9.8±6.1 | −6±1.9 | −3.9±2.8 |
|  | 3 | 179±5.1 | 360±28 | −50±6.5** | 12.7±7.8 | −31±5.8** | 17.8±7.7 | −34±6.2** | 9.4±8.3 | −3±5.8 | 26.8±8.3 |

[Note]
[1] Male SHR used, each consisting of 5 animals
[2] BP : Blood pressure
[3] HR : Heart rate
*:Significantly different from control at a p<0.05
**:Significantly different from control at a p<0.01

Table 3.

Antihypertensive effect (SHR, p.o.)

| Comp. No. | Dose mg./kg. p.o. | Average blood pressure level before administration mmHg | Changes in average blood pressures after administration mmHg 1 hr. | 3 hrs. | 6 hrs. | 24 hrs. |
|---|---|---|---|---|---|---|
| 28 | 1 | 183 | −51 | −31 | −38 | −11 |
|    | 3 | 181 | −74 | −38 | −43 | −15 |
| 29 | 1 | 193 | −25 | −28 | −37 | −17 |

Table 3.-continued
Antihypertensive effect (SHR, p.o.)

| Comp. No. | Dose mg./kg. p.o. | Average blood pressure level before administration mmHg | Changes in average blood pressures after administration mmHg | | | |
|---|---|---|---|---|---|---|
| | | | 1 hr. | 3 hrs. | 6 hrs. | 24 hrs. |
| 30 | 1 | 182 | −13 | −12 | −15 | 0 |
| 31 | 1 | 194 | −22 | −23 | −24 | −6 |
| 33 | 3 | 178 | −15 | −20 | −11 | 3 |
| 34 | 3 | 168 | −20 | −26 | −28 | 0 |
| 35 | 1 | 187 | −27 | −25 | −25 | 0 |
| | 3 | 182 | −45 | −27 | −42 | −2 |
| 36 | 1 | 188 | −18 | −20 | −27 | 3 |
| | 3 | 187 | −47 | −30 | −35 | 0 |
| 37 | 3 | 187 | −18 | −18 | −18 | 5 |
| 38 | 3 | 192 | −18 | −27 | −18 | −2 |
| 39 | 1 | 175 | −18 | −12 | −13 | 3 |
| | 3 | 187 | −65 | −27 | −35 | −15 |
| 41 | 3 | 185 | −6 | −6 | −7 | −2 |
| 42 | 10 | 178 | −23 | −22 | −18 | −3 |
| 43 | 3 | 185 | −40 | −22 | −30 | 8 |
| 44 | 3 | 187 | −28 | −15 | −25 | 3 |
| 45 | 3 | 172 | −9 | −5 | −12 | 0 |
| 46 | 3 | 192 | −20 | −10 | −12 | −8 |
| 47 | 3 | 193 | −22 | −13 | −17 | 2 |
| 48 | 3 | 167 | −9 | 0 | 0 | 2 |
| Prazosin | 1 | 184 | −46 | −37 | −31 | −6 |
| | 3 | 179 | −50 | −31 | −34 | −3 |

It can be seen from the above Tables 1 and 3 that the present quinazoline compounds have a satisfactory antihypertensive action. From the above Table 2, the present quinazoline compound (Compound No. 1) can be seen to show an antihypertensive effect correlated with a dose at 0.3–3 mg./kg. and a duration period from 6 hours up to 24 hours, with the maximum effect being exerted after 3–6 hours from oral administration, whereas prazosin shows the maximum effect after 1 hour from the oral administration and approximately equal antihypertensive effect to that of the present quinazoline compound after 3 hours from the oral administration. Thus, the antihypertensive effect of the present quinazoline compound may be regarded as equal to that of prazosin, but it can be expected that such side-effects as unconsciousness due to a rapid blood pressure depression and others as observed with prazosin in 5 minutes to 1 hour from its administration do less frequently develop in the case of the present quinazoline compound, especially Compound Nos. 1–26. Significant changes in heart rates with the present quinazoline compound and prazosin were not observed as compared with those of control.

B. Adrenergic α-receptor blocking effect

Wistar strain male rats, weighing 250–300 g., were used in this experiment. The rat was anesthetized with pentobarbital sodium and fitted in the right femoral artery with a cannula for determination of blood pressure and in the left femoral vein with another cannula for intravenous injection, the former cannula being connected to an electronic recording system to measure a blood pressure.

Adrenergic α-receptor blocking effect was determined upon whether a hypertensive action with intravenous injection of adrenalin hydrochloride at 0.3 or 1 μg./kg. may be reserved by pretreatment with the test compound.

The results are shown in the following Table 4.

Table 4.
Adrenergic α-receptor blocking effect

| Test compound | Dose (mg./kg.) | α-Receptor blocking effect |
|---|---|---|
| Compound No. 1 | 0.01 | − |
| | 0.1 | + |
| Compound No. 8 | 0.1 | − |
| | 1.0 | + |
| Compound No. 10 | 0.1 | − |
| | 1.0 | + |
| Compound No. 16 | 0.1 | − |
| | 1.0 | + |
| Control (Prazosin) | 0.001 | − |
| | 0.01 | + |

It can be apparent from the above results that the α-receptor blocking actions of the present Compounds No. 1, No. 8, No. 10 and No. 16 are 1/10, 1/100, 1/100 and 1/100, respectively, as compared with the action of prazosin.

C. Acute toxicity

ICR strain male mice, weighing 30–35 g., were deprived of food for 6 hours (water ad libitum) and then used in the experiment. Each group consisted of 8 animals. The test compound was suspended in a 1% tragacanth gum solution so as to be a volume of 40 ml./kg. and orally given. After administration, numbers of deceased animals, changes in body weight and other general states were observed or determined over 1 week.

Survived mice were autopsyed.

The results are shown in the following Table 5.

Table 5.
Acute toxicity in mice

| Test compound | Dose (mg./kg., p.o.) | Body weight before administration (g.) | Body weight gain after 7 days (g.) | No. of deceased animal | LD$_{50}$ (mg./kg., p.o.) |
|---|---|---|---|---|---|
| Compound No. 1 | 1,250 | 31.6 | +3.9 | 0 | |
| | 2,500 | 31.4 | +4.0 | 0 | >5,000 |
| | 5,000 | 31.8 | +4.7 | 0 | |
| Compound No. 28 | 1,250 | 33.9 | +2.6 | 0 | |
| | 2,500 | 32.4 | +3.0 | 0 | >5,000 |
| | 5,000 | 32.1 | +0.2 | 0 | |
| Control (Prazosin) | 1,250 | 31.5 | +2.3 | 0 | |
| | 2,500 | 32.0 | +3.0 | 0 | >5,000 |
| | 5,000 | 32.0 | +3.4 | 0 | |

It is proved that the present quinazoline compound is superior to prazosin in its safety.

From the above-depicted pharmacological and toxicity tests, it is evident that the quinazoline compound of this invention has an excellent antihypertensive activity together with an extremely low toxicity.

The quinazoline compound of this invention is effectively utilizable for preventing and treating various types of hypertension, for example, essential hypertension, renal hypertension, adrenal hypertension, malignant hypertension and so on.

The present quinazoline compound may be administered orally in the form of, e.g., a powder, a fine granule, a granule, a tablet, a pill, a capsule, a solution or a suspension or parenterally in the form of, e.g., an injection or a suppository.

Dosage of the present quinazoline compound may vary depending upon the severity of hypertension to be treated, but a daily dose for adults via oral route is usually in the range of 0.1 to 200 mg., preferably 1–50 mg. The quinazoline compound may be given to patients suffering from hypertension either alone or in combination with any pharmaceutically acceptable carrier. One may optionally determine a ratio of the active compound to the carrier, depending upon the solubility and chemical properties of the active compound applied, the administering route selected and a standard pharmaceutical preparation step. For instance, the active compound may be given in the form of a tablet by the use of an excipient, e.g. lactose, crystalline cellulose, calcium carbonate or dicalcium phosphate, frequently with a glidant, e.g. magnesium stearate, calcium stearate or talc and various disintegrators, e.g. starch, carboxy methyl cellulose or certain silicates. For a capsule, lactose and crystalline cellulose are preferable as an excipient. Where an aqueous suspension is desired, the active compound is blended with an emulsifier and (or) a suspending agent, together with a diluent, e.g. ethanol, propylene glycol, glycerol. For parenteral administration, the active compound may be given in the form of its solution in a suitable solvent, e.g. an injectable glucose solution or a physiological saline solution. Such parenteral solution may be suitably buffered to isotonic, if necessary. For a suppository, there may be usually used caccao butter and polyethylene glycol.

Dose required for lowering blood pressure in patients suffering from hypertension may be determined upon the type and severity of a particular hypertension. In general, it may be practised to initially administer at a small dose and gradually increase doses until the optimum level can be fixed. In case where the active compound is given in the form of a formulation for oral use, it should be employed in a greater amount than that for parenteral use in order to get the same level of antihypertensive activity as developed via parenteral route.

The following reference examples and examples are given for the purpose of illustrating this invention more fully. It should be noted that these reference examples and examples are not to be limiting the scope of this invention.

Reference EXAMPLE 1. Cinnamoylpiperazine

To a solvent mixture of 80 ml. of dioxane and 20 ml. of water were added 7.78 g. of piperazine hexahydrate and 6.89 g. of 47% hydrobromic acid.

To the resulting mixture were added dropwise a solution of 3.33 g. of cinnamoyl chloride in 10 ml. of dioxane while cooling with ice. After the dropwise addition, the resulting solution was stirred for an hour at room temperature and then heated under reflux for an hour.

After the solvents were distilled off under reduced pressure, 50 ml. of ethanol was added and the insoluble substances were filtered off. The ethanol was distilled off under reduced pressure from the filtrate and the 50 ml. of water was added therein. The resulting solution was extracted and washed with ethyl acetate. Then the water layer was made alkaline with 2 N sodium hydroxide and extracted with ethyl acetate again. The combined extracts were dried over anhydrous sodium sulfate and the solvents were distilled off to give 2.60 g. of the desired compound (60% yield).

B.P.: 181°–184° C./2 mmHg
M.P.: 80°–81°
IR (NaCl, cm$^{-1}$): 3330, 1645, 1600

Reference EXAMPLE 2. 2-Methylcinnamoylpiperazin

To 30 ml. of ethanol were added 7.78 g. of piperazine hexahydrate and 6.89 g. of 47% hydrobromic acid to give a homogeneous solution. A solution of 3.61 g. of 2-methylcinnamoyl chloride in 10 ml. of tetrahydrofuran was added dropwise at 0°–20° C. to the resulting solution and the mixture was stirred for 30 minutes. After heating under reflux for an hour, the mixture was cooled with ice to give piperazine hydrobromide as crystals. After the crystals were filtered off, the filtrate was condensed and 40 ml. of 10% hydrochloric acid was added therein. After the resulting mixture was extracted and washed with ethyl acetate, the aqueous phase was alkalized with 5 N sodium hydroxide and extracted with ethyl acetate again. The extract was dried over anhydrous sodium sulfate and condensed to give 3.32 g. of 2-methylcinnamoylpiperazine (72.1% yield).

B.P.: 179°–182° C./0.2 mmHg
IR (NaCl, cm$^{-1}$): 3310, 1640, 1600

Reference EXAMPLE 3.
3-Methoxycinnamoylpiperazine

To a mixture of 3.56 g. of 3-methoxycinnamic acid, 2.02 g. of triethylamine and 20 ml. of ethyl acetate there was added dropwise a solution of 2.60 g. of ethyl chlorocarbonate in 5 ml. of ethyl acetate while cooling with ice. After the dropwise addition, the resulting solution was stirred for two hours at room temperature and the forming triethylamine hydrochloride crystals were filtered off. Then to a solvent mixture of 50 ml. of dioxane and 10 ml. of water were added 3.88 g. of piperazine hexahydrate and 3.45 g. of 47% hydrobromic acid. To this resulting solution was added dropwise while cooled with ice the mixed acid anhydride which was propared beforehand. After stirring overnight at room temperature, the solvents were distilled off under reduced pressure. After the same post-treatment as in Reference 2, 1.20 g. of 3-methoxycinnamoylpiperazine was obtained (24.3% yield).

M.P.: 84°–86° C.
IR (KBr, cm$^{-1}$): 1640, 1590

Reference EXAMPLE 4. Cinnamoylpiperazine

To a solution of 3.88 g. of piperazine hexahydrate in 15 ml. of ethanol was added dropwise with stirring 3.5 g of 47% hydrobromic acid. To the resulting mixture was added gradually 2.78 g. of cinnamic anhydride and the resulting solution was heated under reflux for four hours. After cooling the resulting crystals were filtered off and the filtrate was condensed.

To the residue were added 10% hydrochloric acid and ethyl acetate and then the ethyl acetate layer was removed. The 10% hydrochloric acid solution was neutralized with 10% sodium hydroxide and the resulting solution was extracted with ethyl acetate. After washing with water, the ethyl acetate layer was dried over magnesium sulfate and ethylacetate was distilled off to give 1.09 g. of desired product (50.5% yield). Comparing the infrared spectra, the product obtained was confirmed to be identical with the product obtained in Reference example 1.

Reference EXAMPLE 5.
4-Ethoxycinnamoylpiperazine

From 11.52 g. of 4-ethoxycinnamic acid and 10.71 g. of thionylchloride was prepared 4-ethoxycinnamoyl chloride, a solution of which in tetrahydrofuran was added gradually to a solution of 23.4 g. of piperazine hexahydrate, 20.67 g. of 47% hydrobromic acid and 90 ml. of ethanol. The resulting mixture was stirred overnight at room temperature and cooled with ice, the forming crystals being filtered off. The filtrate was condensed and treated just as in Reference example 1 to obtain 11.23 g. of the desired product (72% yield). The product was treated with concentrated hydrochloric acid to give the corresponding hydrochloride.

M.P.: 214°–215° C. (decomposition) (recrystallized from ethanol)

IR (KBr, cm$^{-1}$): 1640, 1600

Reference EXAMPLE 6.
2,3,4-Trimethoxycinnamoylpiperazine

From 2.38 g. of 2,3,4-trimethoxycinnamic acid and 1.8 g. of thionyl chloride was prepared 2,3,4-trimethoxycinnamoyl chloride, a solution of which in tetrahydrofuran was added gradually to a solution of 3.89 g. of piperazine hexahydrate, 3.49 g. of 47% hydrobromic acid and 15 ml. of ethanol. The reaction was carried out according to the Reference example 1 to give 1.84 g. of oily product (60% yield). The oily product was treated with sulfuric acid to give the corresponding sulfate.

M.P.: 205°–207° C. (decomposition) (recrystallized from methanol)

IR (KBr, cm$^{-1}$): 1636, 1590

Reference EXAMPLE 7.
4-Allyloxycinnamoylpiperazine

From 4.08 g. of 4-allyloxycinnamic acid and 3.57 g. of thionyl chloride was prepared 4-allyloxycinnamoyl chloride, a solution of which in tetrahydrofuran was added gradually to a solution of 7.78 g. of piperazine hexahydrate, 6.89 g. of 47% hydrobromic acid and 30 m. of ethanol. The reaction was carried out according to the Reference example 1 to give 3.28 g. of oily product (75% yield). The product was treated with benzoic acid to give benzoate as crystals.

M.P.: 93°–94° C. (recrystallized from ethanol)

IR (KBr, cm$^{-1}$): 1640, 1620, 1600

Reference EXAMPLES 8–22

In the following table are shown the compounds having the general formulae:

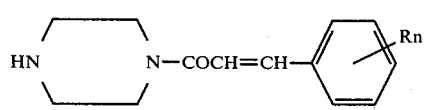

which were synthesized according to the methods described in the Reference examples 8–22.

| Reference example | $R_n$ | B.P., M.P., Refractive index | IR spectrum (cm$^{-1}$) |
|---|---|---|---|
| 8 | —CH₃ (para) | B.P. 182°–185° C./1.5mmHg | 1645,1595 |
| 9 | —CH₃ | M.P. 90°–92° C. | 1640,1595 |
| 10 | —CH(CH₃)₂ | (HCl) M.P. 227–229° C. (decomposition) | 1645,1610 |
| 11 | OCH₃ (ortho) | $n_D^{17.6}$ 1.5871 | 1650,1600 |
| 12 | —OCH₃ (para) | M.P. 250°–252° C. (decomposition) (HCl) | 1650,1600 |
| 13 | OEt (ortho) | M.P. 97°–98° C. | 1645,1595 |
| 14 | —OCH(CH₃)₂ | M.P. 90°–94° C. | 1640,1595 |
| 15 | —OBu | M.P. 225°–226° C. (decomposition) (HCl) | 1645,1600 |
| 16 | 3,4-(OCH₃)₂ | $n_D^{18.5}$ 1.5756 | 1642,1600 |
| 17 | 2,5-(OCH₃)₂ | M.P. 211°–212° C. (decomposition) (HCl) | 1640,1600 |
| 18 | 3,4,5-(OCH₃)₃ | M.P. 129°–131° C. | 1640,1600 |
| 19 | 3,4-methylenedioxy | M.P. 213°–214° C. (decomposition) (HCl) | 1640,1600 |
| 20 | Cl | M.P. 221.5°–224° C. (decomposition) (HCl) | 1650,1608 |
| 21 | —Br | M.P. 205°–208° C. (decomposition) (HCl) | 1650,1608 |
| 22 | naphthyl | M.P. 229°–230° C. (decomposition) (HCl) | 1642,1604 |

Reference EXAMPLE 23.
3-(Furan-2-yl)-acryloylpiperazine

To a homogeneous solution of 15.6 g. (80 mM) of piperazine hexahydrate and 13.8 g. (80 mM) of 47% hydrobromic acid in 40 ml. of ethanol there were added dropwise at room temperature another solution of 6.3 g. (40 mM) of 3-(Furan-2-yl)-acryloylchloride in 10 ml. of tetrahydrofuran. After stirring for two hours at room temperature, the resulting solution was heated at 80° for two hours. Then the solution was cooled with ice and the forming crystals of piperazine hydrobromide were filtered off. The filtrate was condensed under reduced pressure and 80 ml. of 2 N-hydrochloric acid was added into the residue. After neutral substances were removed by extraction with ethyl acetate, the resulting solution was made alkaline with 5 N sodium hydroxide and extracted again with ethyl acetate. After drying over anhydrous sulfate, the combined extracts were condensed to give 4.62 g. of 3-(Furan-2-yl)-acryloylpiperazine (56% yield).

EXAMPLE 1

2-(4-Cinnamoylpiperazin-1-yl)-4-amino-6,7-dimethoxyquinazoline

To 10 ml. of tetrahydrofuran were added 1.2 g. of 2-(piperazin-1-yl)-4-amino-6,7-dimethoxyquinazoline.hydrochloride and 1.33 g. of triethylamine and the resulting mixture was stirred for 30 minutes. Thereafter, 0.66 g. of cinnamoyl chloride was added thereto and the resulting mixture was stirred at room temperature overnight. The crystalline substance thus separated was recovered by filtration, washed thoroughly with water and ethanol and then dried to afford 0.66 g. of the desired product.

M.P.: 245°–248° C.
IR spectrum (KBr, cm$^{-1}$): 1635, 1610, 1585, 1570,
Mass spectrum: m/e: 419 (M+), 233.

EXAMPLE 2

2-[4-(2-Methylcinnamoyl)-piperazin-1-yl]-4-amino-6,7-dimethoxyquinazoline

A mixture of 479 mg. of 2-chloro-4-amino-6,7-dimethoxyquinazoline and 461 mg. of 2-methylcinnamoylpiperazine in 10 ml. of isoamyl alcohol was heated under reflux for 4 hours. After ice-cooling, the reaction mixture was filtered and the product thus obtained was washed with ethanol to yield 812 mg. of the desired product as the hydrochloride.

M.P.: 279°–281° C.
IR spectrum (KBr, cm$^{-1}$): 1640, 1600,
Mass spectrum: m/e: 433 (M+), 233.

EXAMPLE 3

2-[4-(3-Methylcinnamoyl)-piperazin-1-yl]-4-amino-6,7-dimethoxyquinazoline

Following the same procedues as in Example 2, there was obtained the desired product as the hydrochloride.
Yield 85%.
M.P.: 203°–205° C.
IR spectrum (KBr, cm$^{-1}$): 1640, 1600,
Mass spectrum: m/e: 433 (M+), 233.

EXAMPLE 4

2-[4-(4-Methylcinnamoyl)-piperazin-1-yl]-4-amino-6,7-dimethoxyquinazoline

Following the same procedures as in Example 2, there was obtained the desired product as the hydrochloride.
Yield 88%.
M.P.: 252°–254° C.
IR spectrum (KBr, cm$^{-1}$): 1640, 1600,
Mass spectrum: m/e: 433 (M+), 233.

EXAMPLE 5

2-[4-(4-Isopropylcinnamoyl)-piperazin-1-yl]-4-amino-6,7-dimethoxyquinazoline

To a mixture of 342 mg. of 4-isopropylcinnamic acid and 727 mg. of triethylamine in 20 ml. of acetone were added dropwise under ice-cooling 195 mg. of ethyl chlorocarbonate and the resulting mixture was stirred for 3.5 hours. Then, 543 mg. of 2-(piperazin-1-yl)-4-amino-6,7-dimethoxyquinazoline.hydrochloride were added thereto and stirring was continued at room temperature overnight. Then, the acetone was distilled off, the residue was dissolved in 20 ml. of 10% K$_2$CO$_3$ and extracted with ethyl acetate. After drying over magnesium sulfate, the extract was concentrated and recrystallization from methanol gave 361 mg. of the desired product.

M.P.: 237°–238° C.
IR spectrum (KBr, cm$^{-1}$): 1630, 1580, 1560,
Mass spectrum: m/e: 461 (M+), 233.

EXAMPLE 6

2-[4-(2-Methoxycinnamoyl)-piperazin-1-yl]-4-amino-6,7-dimethoxyquinazoline

Following the same procedures as in Example 2, there was obtained the desired product as the hydrochloride.
Yield 82%.
M.P.: 286°–287° C.
IR spectrum (KBr, cm$^{-1}$): 1635, 1595,
Mass spectrum: m/e: 449 (M+), 233.

EXAMPLE 7

2-[4-(3-Methoxycinnamoyl)-piperazin-1-yl]-4-amino-6,7-dimethoxyquinazoline

Following the same procedures as in Example 2, there was obtained the desired product as the hydrochloride.
Yield 52%.
M.P.: 253°–255° C.
IR spectrum (KBr, cm$^{-1}$): 1635, 1590,
Mass spectrum : m/e: 449 (M+), 233.

EXAMPLE 8

2-[4-(4-Methoxycinnamoyl)-piperazin-1-yl]-4-amino-6,7-dimethoxyquinazoline

Following the same procedures as in Example 5, there was obtained the desired product.
Yield 45%.
M.P.: 265°–267° C.
IR spectrum (KBr, cm$^{-1}$): 1640, 1600, 1580,
Mass spectrum: m/e: 449 (M+), 233.

EXAMPLE 9

2-[4-(2-Ethoxycinnamoyl)-piperazin-1-yl]-4-amino-6,7-dimethoxyquinazoline

Following the same procedures as in Example 2, there was obtained the desired product as the hydrochloride.
Yield 90%.
M.P.: 291°–292° C.
IR spectrum (KBr, cm$^{-1}$): 1630, 1590,
Mass spectrum: m/e: 461 (M+), 233.

EXAMPLE 10

2-[4-(4-Ethoxycinnamoyl)-piperazin-1-yl]-4-amino-6,7-dimethoxyquinazoline

To a mixture of 346 mg. of 4-ethoxycinnamic acid and 202 mg. of triethylamine in acetone were added dropwise under ice-cooling 195 mg. of ethyl chlorocarbonate and the resulting mixture was stirred for 3.5 hours. Then, 543 mg. of 2-(piperazin-1-yl)-4-amino-6,7-dimethoxyquinazoline.hydrochloride were added thereto and stirring was continued at room temperature overnight. Thereafter, the crystalline substance thus separated was recovered by filtration and washed successively with water and ethanol to give 430 mg. of the desired product, which was then recrystallized from methanol to afford 300 mg. of the purified product.
M.P.: 277°–278° C.
IR spectrum (KBr, cm$^{-1}$): 1640, 1585, 1570,
Mass spectrum: m/e: 463 (M+), 233.

EXAMPLE 11

2-[4-(4-Butoxycinnamoyl)-piperazin-1-yl]-4-amino-6,7-dimethoxyquinazoline

Following the same procedures as Example 2, there was obtained the desired product as the hydrochloride.
Yield 94%.
M.P.: 237°–238° C.
IR spectrum (KBr, cm$^{-1}$): 1640, 1600,
Mass spectrum: m/e: 491 (M+), 233.

EXAMPLE 12

2-[4-(3,4-Dimethoxycinnamoyl)-piperazin-1-yl]-4-amino-6,7-dimethoxyquinazoline

Following the same procedures as in Example 5, there was obtained the desired product. Yield 42%.
M.P.: 140° C.
IR spectrum (KBr, cm$^{-1}$): 1630, 1580,
Mass spectrum: m/e: 479 (M+), 233.

EXAMPLE 13

2-[4-(3,5-Dimethoxycinnamoyl)-piperazin-1-yl]-4-amino-6,7-dimethoxyquinazoline

Following the same procedures as in Example 5, there was obtained the desired product.
Yield 43%.
M.P.: 132°–135° C.
IR spectrum (KBr, cm$^{-1}$): 1630, 1590, 1570,
Mass spectrum: m/e: 479 (M+), 233.

EXAMPLE 14

2-[4-(2,3,4-Trimethoxycinnamoyl)-piperazin-1-yl]-4-amino-6,7-dimethoxyquinazoline Following the same procedures as in Example 5, there was obtained the desired product.
Yield 40%.
M.P.: 263°–264° C.
IR spectrum (KBr, cm$^{-1}$): 1630, 1580, 1570,
Mass spectrum: m/e: 509 (M+), 233.

EXAMPLE 15

2-[4-(3,4,5-Trimethoxycinnamoyl)-piperazin-1-yl]-4-amino-6,7-dimethoxyquinazoline Following the same procedures as in Example 5, there was obtained the desired product.
Yield 61%.
M.P.: 141°–146° C.
IR spectrum (KBr, cm$^{-1}$): 1630, 1580,
Mass spectrum: m/e: 509 (M+), 233.

EXAMPLE 16

2-[4-(3,4-Methylenedioxycinnamoyl)-piperazin-1-yl]-4-amino-6,7-dimethoxyquinazoline To a solution of 346 mg. of 3,4-methylenedioxycinnamic acid and 364 mg. of triethylamine in 20 ml. of ethyl acetate were added under ice-cooling 195 mg. of ethyl chlorocarbonate and the resulting mixture was then stirred for 4 hours. Then, 543 mg. of 2-(piperazin-1-yl)-4-amino-6,7-dimethoxyquinazoline.hydrochloride were added thereto and the resulting mixture was stirred at room temperature overnight. After 50 ml. of water were added, the precipitate thus separated was recovered by filtration. The resulting crystalline substance was recrystallized from ethanol to give 320 mg. of the desired product as the hydrochloride.
M.P.: 241°–244° C.
IR spectrum (KBr, cm$^{-1}$): 1640, 1600,
Mass spectrum: m/e: 463 (M+), 233.

EXAMPLE 17

2-[4-(4-Allyloxycinnamoyl)-piperazin-1-yl]-4-amino-6,7-dimethoxyquinazoline

Following the same procedures as in Example 10, there was obtained the desired product. Yield 37%.
M.P.: 218°–220° C.
IR spectrum (KBr, cm$^{-1}$): 1635, 1580,
Mass spectrum: m/e: 475 (M+), 233.

EXAMPLE 18

2-[4-(3-nitrocinnamoyl)-piperazin-1-yl]-4-amino-6,7-dimethoxyquinazoline

Following the same procedures as in Example 16, there was obtained the desired product as the hydrochloride.
Yield: 58%.
M.P.: 245°–248° C.
IR spectrum (KBr, cm$^{-1}$): 1640, 1600,
Mass spectrum: m/e: 464 (M+), 233.

EXAMPLE 19

2-[4-(4-Chlorocinnamoyl)-piperazin-1-yl]-4-amino-6,7-dimethoxyquinazoline

Following the same procedures as in Example 16, there was obtained the desired product as the hydrochloride.
Yield 88%.
M.P.: 257°–258° C.
IR spectrum (KBr, cm$^{-1}$): 1635, 1595.
Mass spectrum: m/e: 453 (M+), 233.

EXAMPLE 20

2-[4-(3,4-Dichlorocinnamoyl)-piperazin-1-yl]-4-amino-6,7-dimethoxyquinazoline

Following the same procedures as in Example 10, there was obtained the desired product. Yield 61%.
M.P.: 196°–198° C.
IR spectrum (KBr, cm$^{-1}$): 1630, 1600, 1560,
Mass spectrum: m/e: 487 (M+), 233.

EXAMPLE 21

2-[4-(4-Bromocinnamoyl)-piperazin-1-yl]-4-amino-6,7-dimethoxyquinazoline

Following the same procedures as in Example 2, there was obtained the desired product.
Yield 84%.
M.P.: 266°–268° C.
IR spectrum (KBr, cm$^{-1}$): 1630, 1590,
Mass spectrum: m/e: 497 (M+), 233.

EXAMPLE 22

2-[4-(3-Trifluoromethylcinnamoyl)-piperazin-1-yl]-4-amino-6,7-dimethoxyquinazoline Following the same procedures as in Example 5, there was obtained the desired product.
Yield 47%.

M.P.: 225°–227° C.
IR spectrum (KBr, cm$^{-1}$): 1630, 1580, 1560,
Mass spectrum: m/e: 487 (M$^+$), 233.

EXAMPLE 23

2-[4-(4-Dimethylaminocinnamoyl)-piperazin-1-yl]-4-amino-6,7-dimethoxyquinazoline Following the same procedures as in Example 5, there was obtained the desired product.
Yield 45%.
M.P.: 288°–289° C.
IR spectrum (KBr, cm$^-$): 1640, 1585,
Mass spectrum: m/e: 462 (M$^+$), 233.

EXAMPLE 24

2-[4-(4-Acetyloxycinnamoyl)-piperazin-1-yl]-4-amino-6,7-dimethoxyquinazoline

Following the same procedures as in Example 5, there was obtained the desired product.
Yield 30%.
M.P.: 210°–212° C.
IR spectrum (KBr, cm$^{-1}$: 1765, 1630, 1580,
Mass spectrum: m/e: 477 (M$^+$), 233.

EXAMPLE 25

2-{4-[3-(α-Naphthyl)acryloyl]-piperazin-1-yl}-4-amino-6,7-dimethoxyquinazoline

Following the same procedures as in Example 2, there was obtained the desired product as the hydrochloride.
Yield 72%.
M.P.: 212°–215° C.
IR spectrum (KBr, cm$^{-1}$): 1635, 1600,
Mass spectrum: m/e: 469 (M$^+$), 233.

EXAMPLE 26

2-[4-(4-Isopropyloxy)-piperazin-1-yl]-4-amino-6,7-dimethoxyquinazoline

Following the same procedures as in Example 2, there was obtained the desired product as the hydrochloride.
Yield 89%.
M.P.: 238°–240° C.
IR spectrum (KBr, cm$^-$): 1635, 1595,
Mass spectrum: m/e: 477 (M$^+$), 233.

EXAMPLE 27

2-{4-[3-(Furan-2-yl)-acryloyl]-piperazin-1-yl}-4-amino-6,7-dimethoxyquinazoline

A mixture of 479 mg. (2 mM) of 2-chloro-4-amino-6,7-dimethoxyquinazoline and 412 mg. (2 mM) of 3-(furan-2-yl)-acryloylpiperazine in 10 ml. of isoamyl alcohol was heated under reflux for 4 hours. After ice-cooling, the crystalline substance thus separated was recovered by filtration and washed with ethanol to afford 685 mg. of the desired product as the hydrochloride.
Yield 77%.
M.P.: 245°–247° C. (recrystallized from water-methanol)
IR spectrum (KBr, cm$^{-1}$): 1595,
Mass spectrum: m/e: 409 (M$^+$), 233.

EXAMPLE 28

2-{4-[3-(Furan-3-yl)-acryloyl]-piperazin-1-yl}-4-amino-6,7-dimethoxyquinazoline

To a mixture of 276 mg. (2 mM) of 3-(furan-3-yl)acrylic acid, and 242 mg. (2.4 mM) of triethylamine in 10 ml. of ethyl acetate was added dropwise under ice-cooling a solution of 260 mg. (2.4 mM) of ethyl chlorocarbonate in 5 ml. of ethyl acetate. The resulting mixture was stirred for 3 hours and 761 mg. (2 mM) of 2-piperazine-4-amino-6,7-dimethoxyquinazoline and 484 mg. (4.8 mM) of triethylamine were odded thereto. Stirring was continued at room temperature for further one day. The precipitate thus separated was recovered by filtration and washed well with water to give 480 mg. of the desired product.
Yield 59%.
M.P.: 252°–253° C. (recrystallized from ethanol-water)
IR spectrum (KBr, cm$^{-1}$): 1650, 1590,
Mass spectrum: m/e: 409 (M$^+$), 233.

EXAMPLE 29

2-{4-[3-(5-Methylfuran-2-yl)-acryloyl]-piperazin-1-yl}-4-amino-6,7-dimethoxyquinazoline Following the same procedures as in Example 27 except that 441 mg. of 3-(5-methylfuran-2-yl)-acryloylpiperazine were used instead of the 3-(furan-2-yl)-acryloylpiperazine, there were obtained 756 mg. of the desired product as the hydrochloride.
Yield 81%.
M.P.: 243°–247° C. (recrystallized from methanol-water)
IR spectrum (KBr, cm$^{-1}$): 1635, 1595,
Mass spectrum: m/e: 423 (M$^+$), 233.

EXAMPLE 30

2-{4-[2-Methyl-3-(furan-2-yl)-acryloyl]-piperazin-1-yl}-4-amino-6,7-dimethoxyquinazoline Following the same procedures as in Example 27 except that 440 mg. of 2-methyl-3-(furan-2-yl)-acryloylpiperazine were used instead of the 3-(furan-2-yl)-acryloylpiperazine, there were obtained 750 mg. of the desired product as the hydrochloride.
Yield 82%.
M.P.: 273°–275° C.
IR spectrum (KBr, cm$^{-1}$): 1635, 1595,
Mass spectrum: m/e: 423 (M$^+$), 233.

EXAMPLE 31

2-{4-[3-(5-Nitrofuran-2-yl)-acryloyl]-piperazin-1-yl}-4-amino-6,7-dimethoxyquinazoline Following the same procedures as in Example 28 except that 366 mg. of 3-(5-nitrofuran-2-yl)-acrylic acid were used instead of the 3-(furan-3-yl)-acrylic acid, there were obtained 400 mg. of a crystalline substance, which was then refluxed in ethanol, ice-cooled and recovered by filtration.
Yield 46%.
M.P.: 258°–260° C.
IR spectrum (KBr, cm$^{-1}$): 1635, 1595,
Mass spectrum: m/e: 440 (M$^+$), 233.

Example 32

2-{4-[3-(5-Chlorofuran-2-yl)-acryloyl]-piperazin-1-yl}-4-amino-6,7-dimethoxyquinazoline Following the same procedures as in Example 27 except that 481 mg. of 3-(5-chlorofuran-2-yl)-acryloyl-piperazine were used instead of the 3-(furan-2-yl)acryloylpiperazine, there were obtained 820 mg. of the desired product as the hydrochloride.
Yield 85%.
M.P.: 273°–275° C.
IR spectrum (KBr, cm$^{-1}$): 1635, 1595,
Mass spectrum: m/e: 443 (M+), 233.

Example 33

2-{4-[3-(Thiophen-2-yl)-acryloyl]-piperazin-1-yl}-4-amino-6,7-dimethoxyquinazoline Following the same procedures as in Example 27 except that 445 mg. of 3-(thiophen-2-yl)-acryloylpiperazine were used instead of the 3-(furan-2-yl)-acryloylpiperazine, there were obtained 785 mg. of the desired product as the hydrochloride.
Yield 85%.
M.P.: 226°–228° C.
IR spectrum (KBr, cm$^{-1}$): 1635, 1595
Mass spectrum: m/e: 425 (M+), 233

EXAMPLE 34

2-{4-[3-(Thiophen-3-yl)-acryloyl]-piperazin-1-yl}-4-amino-6,7-dimethoxyquinazoline Following the same procedures as in Example 27 except that 445 mg. of 3-(thiophen-3-yl)-acryloylpiperazine were used instead of the 3-(furan-2-yl)-acryloylpiperazine, there were obtained 744 mg. of the desired product as the hydrochloride.
Yield 81%.
M.P.: 272°–274° C.
IR spectrum (KBr, cm$^{-1}$): 1635, 1595,
Mass spectrum: m/e: 425 (M+), 233.

EXAMPLE 35

2-{4-[3-(3-Methylthiophen-2-yl)-acryloyl]-piperazin-1-yl}-4-amino-6,7-dimethoxyquinazoline Following the same procedures as in Example 27 except that 473 mg. of 3-(3-methylthiophen-2-yl)-acryloylpiperazine were used instead of the 3-(furan-2-yl)acryloylpiperazine, there were obtained 900 mg. of the desired product as the hydrochloride.
Yield 95%.
M.P.: 252°–255° C.
IR spectrum (KBr, cm$^{-1}$): 1630, 1595,
Mass spectrum: m/e: 439 (M+), 233.

EXAMPLE 36

2-{4-[3-(5-Methylthiphen-2-yl)-acryloyl]-piperazin-1-yl}-4-amino-6,7-dimethoxyquinazoline Following the same procedures as in Example 27 except that 473 mg. of 3-(5-methylthiphen-2-yl)-acryloylpiperazine were used instead of the 3-(furan-2-yl)-acryloylpiperazine, there were obtained 800 mg. of the desired product as the hydrochloride.
Yield 84%.
M.P.: 273°–275° C.
IR spectrum (KBr, cm$^{-1}$): 1630, 1590,
Mass spectrum: m/e: 439 (M+), 233.

EXAMPLE 37

2-{4-[2-Methyl-3-(thiophen-2-yl)-acryloyl]-piperazin-1-yl}-4-amino-6,7-dimethoxyquinazoline Following the same procedures as in Example 27 except that 473 mg. of 2-methyl-3-(thiophen-2-yl)-acryloylpiperazine were used instead of the 3-(furan-2-yl)acryloylpiperazine, there were obtained 700 mg. of the desired product as the hydrochloride.
Yield 74%.
M.P.: 272°–274° C.
IR spectrum (KBr, cm$^{-1}$): 1640, 1595,
Mass spectrum: m/e: 439 (M+), 233.

EXAMPLE 38

2-{4-[3-(5-Nitrothiophen-2-yl)-acryloyl]-piperazin-1-yl}-4-amino-6,7-dimethoxyquinazoline Following the same procedures as in Example 27 except that 535 mg. of 3-(5-nitrothiophen-2-yl)-acryloylpiperazine were used instead of the 3-(furan-2-yl)-acryloylpiperazine, there were obtained 466 mg. of the desired product as the hydrochloride. Yield 46%.
M.P.: 279°–283° C.
IR spectrum (KBr, cm$^{-1}$): 1640, 1590,
Mass spectrum: m/e: 470 (M+), 233.

EXAMPLE 39

2-{4-[3-(5-Chlorothiphen-2-yl)-acryloyl]-piperazin-1-yl}-4-amino-6,7-dimethoxyquinazoline Following the same procedures as in Example 27 except that 513 mg. of 3-(5-chlorothiophen-2-yl)-acryloylpiperazine were used instead of the 3-(furan-2-yl)-acryloylpiperazine, there were obtained 825 mg. of the desired product as the hydrochloride.
Yield 83%.
M.P.: 257°–259° C.
IR spectrum (KBr, cm$^{-1}$): 1630, 1590,
Mass spectrum: m/e: 459 (M+), 233.

EXAMPLE 40

2-{4-[3-(Pyridin-2-yl)-acryloyl]-piperazin-1-yl}-4-amino-6,7-dimethoxyquinazoline Following the same procedures as in Example 28 except that 298 mg. of 3-(pyridin-2-yl)-acrylic acid were used instead of the 3-(furan-3-yl)-acrylic acid, there were obtained 174 mg. of the desired product.
Yield 21%.
M.P.: 235°–237° C. (recrystallized from methanol)
IR spectrum (KBr, cm$^{-1}$): 1640, 1590,
Mass spectrum: m/e: 420 (M+), 233.

EXAMPLE 41

2-{4-[3-(3-Pyridin-3-yl)-acryloyl]-piperazin-1-yl}-4-amino-6,7-dimethoxyquinazoline Following the same procedures as in Example 28 except that 298 mg. of 3-(pyridin-3-yl)-acrylic acid were used instead of the 3-(furan-3-yl)-acrylic acid, there were obtained 450 mg. of the desired product.
Yield 54%.
M.P.: 279°–281° C. (recrystallized from ethanol-water)
IR spectrum (KBr, cm$^{-1}$): 1630, 1570,
Mass spectrum: m/e: 420 (M+), 233.

EXAMPLE 42

2-55-4-[3-(Pyridin-4-yl)-acryloyl]-piperazin-1-yl}-4-amino-6,7-dimethoxyquinazoline Following the same procedures as in Example 28 except that 298 mg. of 3-(pyridin-4-yl)-acrylic acid were used instead of the 3-(furan-3-yl)-acrylic acid, there were obtained 450 mg. of the desired product.

Yield 54%.

M.P.: 275°–276° C. (recrystallized from ethanol-water)

IR spectrum (KBr, cm$^{-1}$): 1645, 1625, 1610, 1560,

Mass spectrum: m/e: 420 (M+), 233.

EXAMPLE 43

2-{4-[3-(Furan-2-yl)-acryloyl]-homopiperazin-1-yl}-4-amino-6,7-dimethoxyquinazoline Following the same procedures as in Example 27 except that 440 mg. of 3-(furan-2-yl)-acryloylhomopiperazine were used instead of the 3-(furan-2-yl)-acryloyl-piperazine, there were obtained 750 mg. of the desired product as the hydrochloride.

Yield 82%.

M.P.: 201°–203° C. (recrystallized from ethanol)

IR spectrum (KBr, cm$^{-1}$): 1640, 1600,

Mass spectrum: m/e: 423 (M+), 233.

EXAMPLE 44

2-{4-{3-(Thiophen-2-yl)-acryloyl]-homopiperazin-1-yl}-4-amino-6,7-dimethoxyquinazoline Following the same procedures as in Example 27 except that 474 mg. of 3-(thiophen-2-yl)-acryloyl-homopiperazine were used instead of the 3-(furan-2-yl)-acryloylpiperazine, there were obtained 791 mg. of the desired product as the hydrochloride.

Yield 83%.

M.P.: 240°–241° C.

IR spectrum (KBr, cm$^{-1}$): 1635, 1600,

Mass spectrum: m/e: 439 (M+), 233.

EXAMPLE 45.

2-{4-[3-(Pyridin-3-yl)-acryloyl]-homopiperazin-1-yl}-4-amino-6,7-dimethoxyquinazoline A mixture of 383 mg. of 2-homopiperazine-4-amino-6,7-dimethoxyquinazoline.hydrochloride and 608 mg. of 1,8-diazabicyclo[5.4.0]undecene-7 in 30 ml. of ethyl acetate was stirred at room temperature. Then, 245 mg. of 3-(pyridin-3-yl)-acryloyl chloride were added thereto at room temperature, stirring was continued for 1 hour and then reflux was effected for an additional 1 hour. After completion of the reaction, the reaction mixture was extracted with ethyl acetate, the extract was washed with water, dried over magnesium sulfate and the solvent distilled off to give 273 mg. of the desired product as crystals.

Yield 63%.

M.P.: 141°–143° C.

IR spectrum (KBr, cm$^{-1}$): 1630, 1590,

Mass spectrum: m/e: 434 (M+), 233.

We claim:

1. A compound having the formula

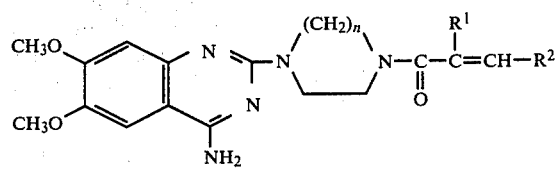

wherein
R$^1$ is a hydrogen atom or an alkyl group having 1–5 carbon atoms;
R$^2$ is a group of the formula

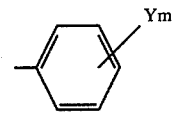

in which Y is a hydrogen atom, an alkyl group of 1–5 carbon atoms, an alkoxy group of 1–5 carbon atoms, an alkenyloxy group, a methylenedioxy group, a nitro group, a halogen atom, a trifluoromethyl group, an acyloxy group, a hydroxy group, an unsubstituted or substituted amino group or a condensed benzene nucleus and m is an integer of 1–3 inclusive, or a group of the formula

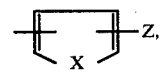

in which X is an oxygen atom, a sulfur atom or a carbon-nitrogen double bond and Z is a hydrogen atom, an alkyl group of 1–5 carbon atoms, an alkoxy group of 1–5 carbon atoms, a nitro group or a halogen atom; and
n is an integer of 2–3 inclusive;
provided that, when R$^2$ is the said group

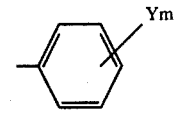

n is 2 and R$^1$ is a hydrogen atom or, when R$^2$ is the said group;

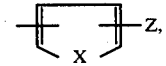

n is 2 or 3 and R$^1$ is a hydrogen atom or the said alkyl group and a pharmaceutically acceptable acid addition salt thereof.

2. A compound according to claim 1 wherein R$^1$ is a hydrogen atom, R$^2$ is a group of the formula

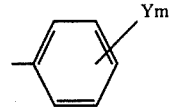

in which Y is a hydrogen atom, an alkyl group of 1–5 carbon atoms, an alkoxy group of 1–5 carbon atoms, an alkenyloxy group, a methylenedioxy group, a nitro group, a halogen atom, a trifluoromethyl group, an acyloxy group, a hydroxy group, an unsubstituted or substituted amino group or a condensed benzene nucleus and m is an integer of 1–3 inclusive and n is 2.

3. A compound according to claim 1 wherein $R^1$ is a hydrogen atom or an alkyl group having 1–5 carbon atoms, $R^2$ is a group of the formula $$\underset{X}{\boxed{\phantom{xx}}}-Z,$$

in which X is an oxygen atom, a sulfur atom or a carbon-nitrogen double bond and Z is a hydrogen atom, an alkyl group of 1–5 carbon atoms, an alkoxy group of 1–5 carbon atoms, a nitro group or a halogen atom and n is an integer of 2–3 inclusive.

4. A compound according to claim 2 wherein said compound is 2-(4-cinnamoylpiperazin-1-yl)-4-amino-6,7-dimethoxyquinazoline.

5. A compound according to claim 2 wherein said compound is 2-[4-(2-methylcinnamoyl)-piperazin-1-yl]-4-amino-6,7-dimethoxyquinazoline.

6. A compound according to claim 2 wherein said compound is 2-[4-(3-methylcinnamoyl)-piperazin-1-yl]-4-amino-6,7-dimethoxyquinazoline.

7. A compound according to claim 2 wherein said compound is 2-[4-(4-methylcinnamoyl)-piperazin-1-yl]-4-amino-6,7-dimethoxyquinazoline.

8. A compound according to claim 2 wherein said compound is 2-[4-(4-isopropylcinnamoyl)-piperazin-1-yl]-4-amino-6,7-dimethoxyquinazoline.

9. A compound according to claim 2 wherein said compound is 2-[4-(3-methoxycinnamoyl)-piperazin-1-yl]-4-amino-6,7-dimethoxyquinazoline.

10. A compound according to claim 2 wherein said compound is 2-[4-(4-methoxycinnamoyl)-piperazin-1-yl]-4-amino-6,7-dimethoxyquinazoline.

11. A compound according to claim 2 wherein said compound is 2-[4-(4-ethoxycinnamoyl)-piperazin-1-yl]-4-amino-6,7-dimethoxyquinazoline.

12. A compound according to claim 2 wherein said compouns is 2-[4-(3,5-dimethoxycinnamoyl)-piperazin-1-yl]-4-amino-6,7-dimethoxyquinazoline.

13. A compound according to claim 2 wherein said compound is 2-[4-(2,3,4-trimethoxycinnamoyl)-piperazin-1-yl]-4-amino-6,7-dimethoxyquinazoline.

14. A compound according to claim 2 wherein said compound is 2-[4-(3,4-methylenedioxycinnamoyl)-piperazin-1-yl]-4-amino-6,7-dimethoxyquinazoline.

15. A compound according to claim 2 wherein said compound is 2-[4-(4-allyloxycinnamoyl)-piperazin-1-yl]-4-amino-6,7-dimethoxyquinazoline.

16. A compound according to claim 2 wherein said compound is 2-[4-(4-bromocinnamoyl)-piperazin-1-yl]-4-amino-6,7-dimethoxyquinazoline.

17. A compound according to claim 2 wherein said compound is 2-[4-(3-trifluoromethylcinnamoyl)-piperazin-1-yl]-4-amino-6,7-dimethoxyquinazoline.

18. A compound according to claim 2 wherein said compound is 2-[4-(4-dimethylaminocinnamoyl)-piperazin-1-yl]-4-amino-6,7-dimethoxyquinazoline.

19. A compound according to claim 3 wherein said compound is 2-{4-[3-(furan-2-yl)-acryloyl]-piperazin-1-yl}-4-amino-6,7-dimethoxyquinazoline.

20. A compound according to claim 3 wherein said compound is 2-{4-[3-(furan-3-yl)-acryloyl]-piperazin-1-yl}-4-amino-6,7-dimethoxyquinazoline.

21. A compound according to claim 3 wherein said compound is 2-{4-[3-(5-methylfuran-2-yl)-acryloyl]-piperazin-1-yl}-4-amino-6,7-dimethoxyquinazoline.

22. A compound according to claim 3 wherein said compound is 2-{4-[2-methyl-3-(furan-2-yl)-acryloyl]-piperazin-1-yl}-4-amino-6,7-dimethoxyquinazoline.

23. A compound according to claim 3 wherein said compound is 2-{4-[3-(5-nitrofuran-2-yl)-acryloyl]-piperazin-1-yl}-4-amino-6,7-dimethoxyquinazoline.

24. A compound according to claim 3 wherein said compound is 2-{4-[3-(5-chlorofuran-2-yl)-acryloyl]-piperazin-1-yl}-4-amino-6,7-dimethoxyquinazoline.

25. A compound according to claim 3 wherein said compound is 2-{4-[3-(thiophen-2-yl)-acryloyl]-piperazin-1-yl}-4-amino-6,7-dimethoxyquinazoline.

26. A compound according to claim 3 wherein said compound is 2-{4-[3-(thiophen-3-yl)-acryloyl]-piperazin-1-yl}-4-amino-6,7-dimethoxyquinazoline.

27. A compound according to claim 3 wherein said compound is 2-{4-[3-(3-methylthiophen-2-yl)-acryloyl]-piperazin-1-yl}-4-amino-6,7-dimethoxyquinazoline.

28. A compound according to claim 3 wherein said compound is 2-{4-[3-(5-methylthiophen-2-yl)-acryloyl]-piperazin-1-yl}-4-amino-6,7-dimethoxy-quinazoline 29. A compound according to claim 3 wherein said compound is 2-{4-[2-methyl-3-(thiophen-2-yl)-acryloyl]-piperazin-1-yl}-4-amino-6,7-dimethoxyquinazoline.

30. A compound according to claim 3 wherein said compound is 2-{4-[3-(5-nitrothiophen-2-yl)-acryloyl]-piperazin-1-yl}-4-amino-6,7-dimethoxyquinazoline.

31. A compound according to claim 3 wherein said compound is 2-{4-[3-(5-chlorothiophen-2-yl)-acryloyl]-piperazin-1-yl}-4-amino-6,7-dimethoxyquinazoline.

32. A compound according to claim 3 wherein said compound is 2-{4-[3-(pyridin-2-yl)-acryloyl]-piperazin-1-yl}-4-amino-6,7-dimethoxyquinazoline.

33. A compound according to claim 3 wherein said compound is 2-{4-[3-(pyridin-3-yl)-acryloyl]-piperazin-1-yl}-4-amino-6,7-dimethoxyquinazoline.

34. A compound according to claim 3 wherein said compound is 2-{4-[3-(pyridin-4-yl)-acryloyl]-piperazin-1-yl}-4-amino-6,7-dimethoxyquinazoline.

35. A compound according to claim 3 wherein said compound is 2-{4-[3-(furan-2-yl)-acryloyl]-homopiperazin-1-yl}-4-amino-6,7-dimethoxyquinazoline.

36. A compound according to claim 3 wherein said compound is 2-{4-[3-(thiophen-2-yl)-acryloyl]-homopiperazin-1-yl}-4-amino-6,7-dimethoxyquinazoline.

37. A compound according to claim 3 wherein said compound is 2-{4-[3-(pyridin-3-yl)-acryloyl]-homopiperazin-1-yl}-4-amino-6,7-dimethoxyquinazoline.

38. An antihypertensive composition which comprises as an active ingredient an effective amount of (i) a compound having the formula wherein
R¹ is a hydrogen atom or an alkyl group having 1–5 carbon atoms;
R² is a group of the formula

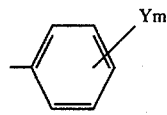

in which Y is a hydrogen atom, an alkyl group of 1–5 carbon atoms, an alkoxy group of 1–5 carbon atoms, an alkenyloxy group, a methylenedioxy group, a nitro group, a halogen atom, a trifluoromethyl group, an acyloxy group, a hydroxygroup, an unsubstituted or substituted amino group or a condensed benzene nucleus and m is an integer of 1–3 inclusive, or a group of the formula

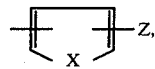

in which X is an oxygen atom, a sulfur atom or a carbon-nitrogen double bond and Z is a hydrogen atom, an alkyl group of 1–5 carbon atoms, an alkoxy group of 1–5 carbon atoms, a nitro group or a halogen atom; and
n is an integer of 2–3 inclusive;
provided that, when R² is the said group

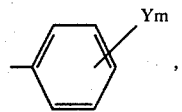

n is 2 and R¹ is a hydrogen atom or, when R² is the said group

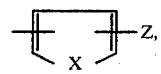

n is 2 or 3 and R¹ is a hydrogen atom or the said alkyl group or (ii) a pharmaceutically acceptable acid addition salt thereof; and a pharmaceutically acceptable carrier.

* * * * *

UNITED STATES PATENT AND TRADEMARK OFFICE
CERTIFICATE OF CORRECTION

PATENT NO. : 4,189,484
DATED : February 19, 1980
INVENTOR(S) : SUSUMU MIZOGAMI et al It is certified that error appears in the above-identified patent and that said Letters Patent are hereby corrected as shown below:

Column 2, line 65: before "new", insert ---a---.

Column 6, lines 56-57: replace "4-isopropylcinnamaylpiper" with ---4-isopropylcinnamoylpiperazine---.

Column 6, line 57: replace "2-methoxypiperazine" with ---2-methoxycinnamoylpiperazine---.

Column 6, lines 60-61: replace "4-butoxycinnoylpiperazine" with ---4-butoxycinnamoylpiperazine---.

Column 6, line 62: replace "3,5-dimethoxycinnoulpiperazine" with ---3,5-dimethoxycinnamoylpiperazine---.

Column 6, line 63: replace "3,4,5-trimethoxycinnomayl-piperazine" with ---3,4,5-trimethoxycinnamoylpiperazine---.

Column 6, lines 64-65: replace "4-allyloxycinnomayl-piperazine" with ---4-allyloxycinnamoylpiperazine---.

Column 6, line 66: replace "4-bromocinnamylpiperazine" with ---4-bromocinnamoylpiperazine---.

Column 8, line 30: insert ---(XI)--- below the section of formula: 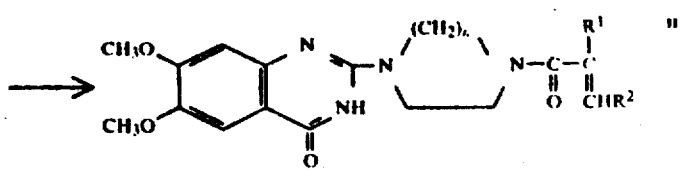

UNITED STATES PATENT AND TRADEMARK OFFICE
CERTIFICATE OF CORRECTION

PATENT NO. : 4,189,484
DATED : February 19, 1980
INVENTOR(S) : SUSUMU MIZOGAMI et al It is certified that error appears in the above-identified patent and that said Letters Patent are hereby corrected as shown below:

Columns 9-10, Table 2: in the seventh column, under the heading "$\frac{BP}{(mm.Hg.)}$", second line, replace "$-16\pm3.3**$" with --- $-16\pm3.3*$ ---.

Column 21, line 49: replace "(KBr, $cm^-$)" with ---(KBr, $cm^{-1}$)---.

Column 25, line 3: replace "2-55-4-[3..." with ---2-{4-[3... ---.

Signed and Sealed this

*Twenty-third* Day of *December 1980*

[SEAL]

*Attest:*

SIDNEY A. DIAMOND

*Attesting Officer*

*Commissioner of Patents and Trademarks*